United States Patent
De Brueker et al.

(10) Patent No.: US 9,980,989 B2
(45) Date of Patent: May 29, 2018

(54) BACTERIAL COMPOSITION FOR THE TREATMENT OF COLIBACILLOSIS ON FARMS, IN PARTICULAR POULTRY FARMS, AND ALSO DRINKING WATER CONTAINING SUCH A BACTERIAL COMPOSITION

(71) Applicant: NOLIVADE, Change (FR)

(72) Inventors: Marc De Brueker, Change (FR); Stéphane Thebault, Germain le Fouilloux (FR)

(73) Assignee: NOLIVADE, Change (FR)

( * ) Notice: Subject to any disclaimer, the term of this patent is extended or adjusted under 35 U.S.C. 154(b) by 556 days.

(21) Appl. No.: 14/404,266

(22) PCT Filed: May 29, 2013

(86) PCT No.: PCT/FR2013/051202
§ 371 (c)(1),
(2) Date: May 18, 2015

(87) PCT Pub. No.: WO2013/178947
PCT Pub. Date: Dec. 5, 2013

(65) Prior Publication Data
US 2015/0250832 A1    Sep. 10, 2015

(30) Foreign Application Priority Data
May 30, 2012 (FR) .................................. 12 54976

(51) Int. Cl.
| | |
|---|---|
| A61K 35/74 | (2015.01) |
| A61K 35/744 | (2015.01) |
| A61K 39/07 | (2006.01) |
| A61K 39/09 | (2006.01) |
| A23L 2/38 | (2006.01) |
| A23L 2/52 | (2006.01) |
| A61K 35/742 | (2015.01) |
| A23K 10/18 | (2016.01) |
| A23K 50/00 | (2016.01) |
| A23K 50/75 | (2016.01) |
| A61K 39/00 | (2006.01) |

(52) U.S. Cl.
CPC ............ *A61K 35/744* (2013.01); *A23K 10/18* (2016.05); *A23K 50/00* (2016.05); *A23K 50/75* (2016.05); *A23L 2/38* (2013.01); *A23L 2/52* (2013.01); *A61K 35/742* (2013.01); *A61K 39/07* (2013.01); *A61K 39/09* (2013.01); *A23V 2002/00* (2013.01); *A61K 2039/52* (2013.01); *A61K 2039/542* (2013.01); *A61K 2039/552* (2013.01); *A61K 2039/70* (2013.01)

(58) Field of Classification Search
None
See application file for complete search history.

(56) References Cited

U.S. PATENT DOCUMENTS

| | | |
|---|---|---|
| 2002/0146399 A1 | 10/2002 | Raczek |
| 2011/0287157 A1 | 11/2011 | Watson |

FOREIGN PATENT DOCUMENTS

| | | |
|---|---|---|
| KR | 20110125810 A | 11/2011 |
| WO | WO9212639 A1 | 8/1992 |

OTHER PUBLICATIONS

IPRP dated Dec. 2, 2014 in corresponding International Application No. PCT/FR2013/051202.
Kyriakis et al., "The Effect of Probiotic LSP 122 on the Control of Post-Weaning Diarrhea Syndrome of Piglets", Research in Veterinary Science, British Veterinary Association, London, vol. 67, No. 3, Jan. 1, 1999 (XP008003110).
Teo et al., "Inhibition of Clostridium perfringens by a novel strain of Bacillus subtilis isolated from the gastrointestinal tracts of healthy chickens", Applied and Environmental Microbiology, American Society for Microbiology, US, vol. 71, No. 8, Aug. 1, 2005 (XP002375508).
Maneewan et al., "Development of Bacillus subtilis MP and effective utilization on productivity and microorganisms in feces of suckling piglets", International Journal of Applied Res. Veterinary Medicine, vol. 9, No. 4, 2011 (XP002688379).

*Primary Examiner* — Suzanne M Noakes
*Assistant Examiner* — Stephen M Chong
(74) *Attorney, Agent, or Firm* — Faegre Baker Daniels LLP

(57) ABSTRACT

A bacterial composition for the treatment of colibacillosis on farms, in particular poultry farms, contains at least $10^5$ cfu/ml of at least one of the following four strains of *Bacillus subtilis* or of *Bacillus licheniformis*: NOL01, NOL02, NOL03 and NOL04, and at least $10^5$ cfu/ml of at least one lactic acid bacterium chosen from the following lactic acid bacteria: *Lactococcus lactis* spp *lactis* 1 strain NOL11 and *Pediococcus pentosaceus* 2 strain NOL12.

15 Claims, 3 Drawing Sheets

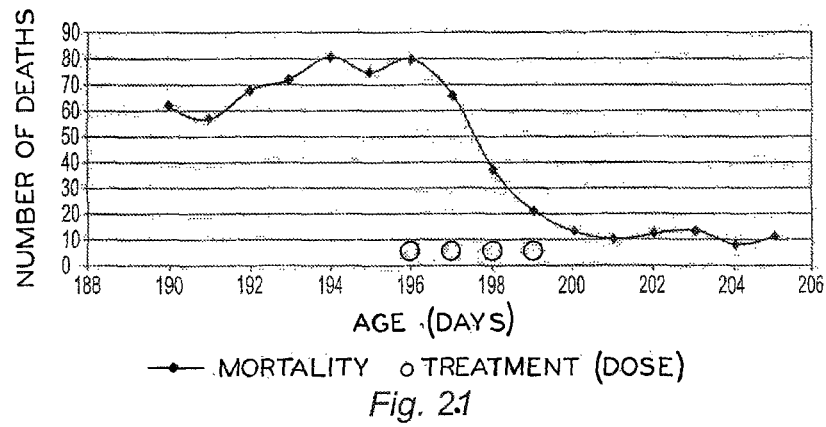
Fig. 2.1
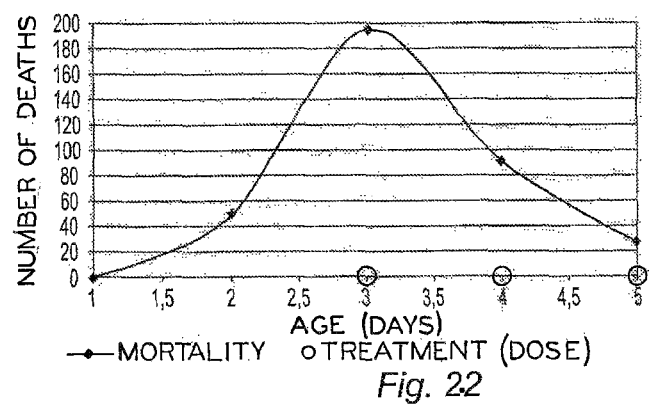
Fig. 2.2

BACTERIAL COMPOSITION FOR THE TREATMENT OF COLIBACILLOSIS ON FARMS, IN PARTICULAR POULTRY FARMS, AND ALSO DRINKING WATER CONTAINING SUCH A BACTERIAL COMPOSITION

CROSS-REFERENCE TO RELATED APPLICATIONS

This application is a U.S. National Phase Patent Application based on International Application No. PCT/FR2013/051202 filed May 29, 2013, which claims priority to French Patent Application No. 1254976 filed May 30, 2012, the entire disclosures of which are hereby explicitly incorporated by reference herein.

BACKGROUND OF THE INVENTION

1. Field of the Invention

The present invention relates to a bacterial composition for the treatment of colibacillosis on animal farms, in particular poultry farms.

2. Description of the Related Art

Poultry is the second most widely consumed meat in the world, with more than 91 million tonnes being consumed in 2009.

French production amounts to about 1,650,000 tonnes CWE (carcass weight equivalent), 50% of which is chicken, which is considerable.

Infection by the bacterium *Escherichia coli*, which represents a very large proportion of bacterial infections in poultry, constitutes a real plague for poultry farmers and can lead to very considerable economic losses.

In birds, the bacterium *Escherichia coli* generally corresponds to an opportunistic contaminating agent which creates infections in the presence of various contaminating factors: intensive farming technique, farming conditions (inadequacy in terms of the management of water quality, ventilation, heating, etc.), presence of viruses or of various pathogenic bacteria, etc.

These contaminating factors lead to weakening and immunodepression of the animals, allowing *E. coli* to infect them, with all the harmful consequences that result.

In order to combat this plague, poultry farmers endeavour to take as many systematic preventive measures as possible in order to ensure on their farms strict hygiene conditions which will prevent as far as possible the development of pathogenic germs, to that end, they in particular carry out regular cleaning and disinfection operations on their premises, especially during periods of depopulation.

Another essential requirement for combating the development of pathogenic germs consists in ensuring that the drinking water for the poultry is always of impeccable quality, even and especially in the drinking troughs.

In parallel with these preventive treatments, the only curative treatment currently proposed to poultry farmers for treating colibacillosis which has already been declared is antibiotic therapy, which has many disadvantages.

First of all, such a treatment is increasingly difficult to prescribe owing to the early slaughter of the animals, considerable waiting times, etc.

However, the main disadvantage of antibiotic treatment in veterinary medicine is linked to the increasing phenomena of antibiotic resistance: consequently, in order not to foster the emergence of germs which are resistant to multiple antibiotics, health authorities are currently very vigilant regarding the use of antibiotics on farms, and for that reason, the use of some antibiotics may even be limited or even prohibited in the shorter or longer term.

It would therefore be desirable to be able to propose to poultry farmers a means of treating already declared colibacillosis which can constitute an alternative to antibiotic therapy.

SUMMARY OF THE INVENTION

The present invention provides a bacterial composition for the treatment of colibacillosis on animal farms, in particular poultry farms. The composition includes at least $10^5$ cfu/ml of at least one of the following four strains of *Bacillus subtilis* or *Bacillus licheniformis*: NOL01, NOL02, NOL03 and NOL04, together with at least $10^5$ cfu/ml of at least one lactic acid bacterium chosen from the following lactic acid bacteria: *Lactococcus lactis* spp *lactis* 1 strain NOL11 and *Pediococcus pentosaceus* 2 strain NOL12.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 2.1 is a graph illustrating change in mortality in accordance with Example 2.1;

FIG. 2.2 is a graph illustrating change in mortality in accordance with Example 2.2.

FIG. 2.3 is a graph illustrating change in mortality in accordance with Example 2.3; and FIG. 2.4 is a graph illustrating change in mortality in accordance with Example 2.4.

Figure 1:
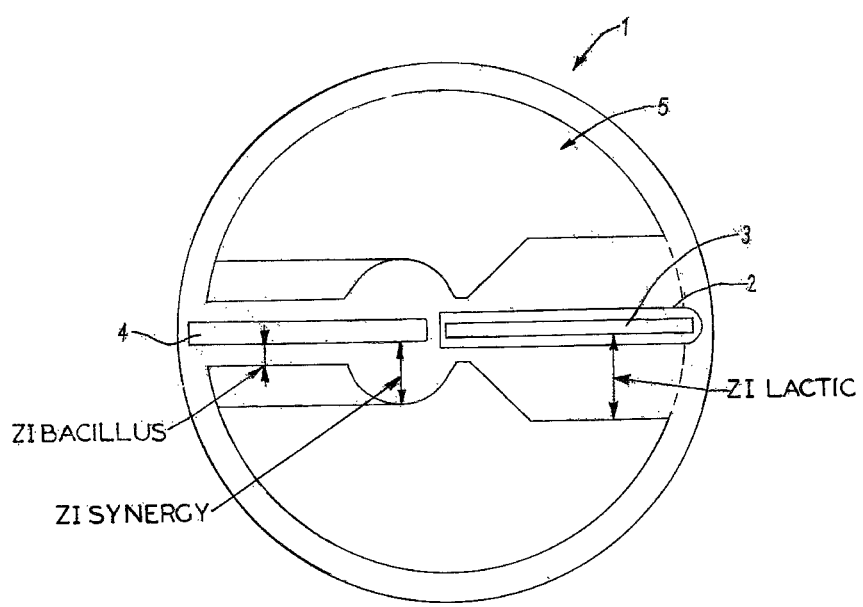
FIG. 1 is a schematic view of a Petri dish in accordance with Example 1.
Figure 23:
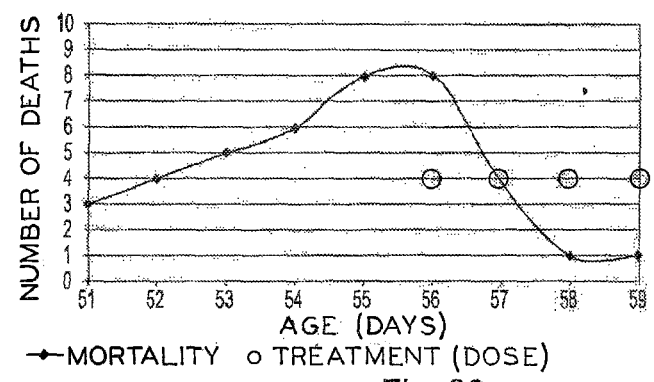
Figure 24:
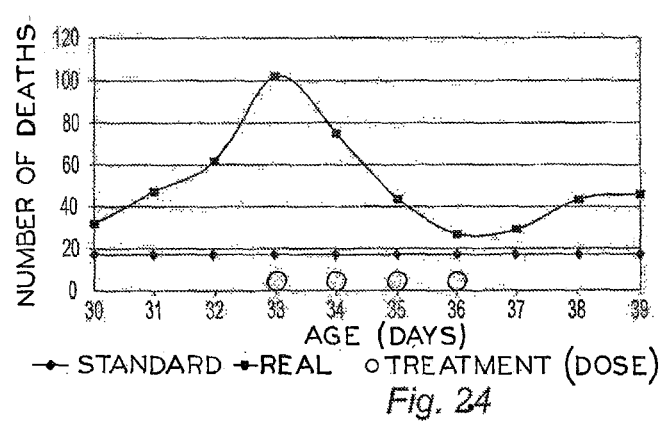

Corresponding reference characters indicate corresponding parts throughout the several views. Although the exemplifications set out herein illustrate embodiments of the invention, the embodiments disclosed below are not intended to be exhaustive or to be construed as limiting the scope of the invention to the precise forms disclosed.

DETAILED DESCRIPTION

Within the above-mentioned context, it has been found according to the invention that farmers, and in particular poultry farmers, use various bacterial compositions comprising in particular bacteria of the genus *bacillus* for cleaning and disinfecting their premises, especially during periods of depopulation.

It has also been established that bacteria are able to act as probiotics by colonising the digestive tract of animals so as to prevent the development therein of pathogenic bacteria such as *E. coli*.

However, it was thought that some strains of bacteria, especially bacteria of the genus *bacillus*, may have, in addition to their probiotic properties, also curative properties for the treatment of colibacillosis which has already taken hold, and empirical research has been carried out in an attempt to isolate such strains.

It has thus been possible to establish, according to the invention, that, very surprisingly, particular strains of *Bacillus subtilis* or *Bacillus licheniformis* can act in synergy with certain strains of lactic acid bacteria in order to inhibit the development of colibacilli in poultry.

Consequently, the present invention relates to a bacterial composition for the treatment of colibacillosis on animal farms, in particular poultry farms, characterised in that it comprises on the one hand at least $10^5$ cfu/ml of at least one of the following four strains of *Bacillus subtilis* or *Bacillus licheniformis*: NOL 01, NOL 02, NOL 03 and NOL 04, and on the other hand at least $10^5$ cfu/ml of at least one lactic acid bacterium chosen from the following lactic acid bacteria: *Lactococcus lactis* spp *lactis* 1 strain NOL 11 and *Pediococcus pentosaceus* 2 strain NOL 12.

The composition according to the invention can advantageously comprise between $10^5$ and $10^9$ cfu/ml of *bacillus* and between $10^9$ and $10^{10}$ cfu/ml of lactic acid bacteria.

This composition is to be added to the drinking water of the farm animals, in particular poultry.

The invention accordingly relates also to drinking water for farm animals, in particular for poultry, characterised in that it comprises the above-mentioned bacterial composition.

By way of example, the drinking water can comprise the bacterial composition in an amount of from 10 to 100 ml in 1000 l.

The composition provided by the invention can be proposed in the form of doses which comprise bacteria in sporulated and/or vegetative form and which are in any form, especially frozen doses and/or doses which have undergone freeze-drying or atomization treatment.

It has been possible to establish that, in a composition comprising bacilli in sporulated form, a large proportion of spores can be returned to the vegetative state and therefore become active again in the digestive tract of the poultry.

The bacterial strains which can be contained in the composition provided by the invention have been identified by their morphology and also by their biological and biochemical characteristics.

The results of this identification are mentioned below.

1/Strain: NOL 01

Genus and species: *Bacillus subtilis* or *licheniformis*
Morphology: Long gram+ *bacillus* in a small chain
Characteristics:
  Culture medium: basic (PCA) or blood agar
  Temperature: 30-37° C.
  Appearance of the colonies on blood agar and PCA:
    Young and isolated colonies: convex, glistening
Oxidase test+
Catalase test+

API 50CHB Profile

| | Test | Result |
|---|---|---|
| 1 | Glycerol | + |
| 2 | Erythritol | − |
| 3 | D-Arabinose | − |
| 4 | L-Arabinose | + |
| 5 | D-Ribose | + |
| 6 | D-Xylose | + |
| 7 | L-Xylose | − |
| 8 | D-Adonitol | − |
| 9 | Methyl βD-xylopyranoside | − |
| 10 | D-Galacyose | − |
| 11 | D-Glucose | + |
| 12 | D-Fructose | + |
| 13 | D-Mannose | + |
| 14 | L-Sorbose | − |
| 15 | L-Rhamnose | − |
| 16 | Dulcitol | − |
| 17 | Inositol | + |
| 18 | D-Mannitol | + |
| 19 | D-Sorbitol | + |
| 20 | Methyl αD-mannopyranoside | − |
| 21 | Methyl αD-glucopyranoside | + |
| 22 | N-Acetylglucosamine | − |
| 23 | Amygdalin | + |
| 24 | Arbutin | + |
| 25 | Aesculin iron citrate | + |
| 26 | Salicin | + |
| 27 | D-Cellobiose | + |
| 28 | D-Maltose | + |
| 29 | D-Lactose | − |
| 30 | D-Melibiose | + |
| 31 | D-Saccharose | + |
| 32 | D-Trehalose | + |
| 33 | Inulin | + |
| 34 | D-Melezitose | − |
| 35 | D-Raffinose | + |
| 36 | Starch | + |
| 37 | Glycogen | + |
| 38 | Xylitol | − |
| 39 | Gentiobiose | − |
| 40 | D-Turanose | − |
| 41 | D-Lyxose | − |
| 42 | D-Tagatose | − |
| 43 | D-Fucose | − |
| 44 | L-Fucose | − |
| 45 | D-Arabitol | − |
| 46 | L-Arabitol | − |
| 47 | Potassium gluconate | − |
| 48 | Potassium 2-cetogluconate | − |
| 49 | Potassium 5-cetogluconate | − |

2/Strain: NOL 02

Genus and species: *Bacillus subtilis*
Morphology: Gram+ *bacillus* isolated or in twos. Presence of spores.
Characteristics:
  Culture medium: basic (PCA) or blood agar
  Temperature: 30-37° C.
  Appearance of the colonies on PCA:
    large, flat, round, thy, anchored in the agar
  Appearance of the colonies on blood agar:
    non-haemolytic, floury contour
Oxidase test+
Catalase test+

API 50CHB Profile

| | Test | Result |
|---|---|---|
| 1 | Glycerol | + |
| 2 | Erythritol | − |
| 3 | D-Arabinose | − |
| 4 | L-Arabinose | + |
| 5 | D-Ribose | + |
| 6 | D-Xylose | − |
| 7 | L-Xylose | − |
| 8 | D-Adonitol | − |
| 9 | Methyl βD-xylopyranoside | − |
| 10 | D-Galacyose | − |
| 11 | D-Glucose | + |
| 12 | D-Fructose | + |

-continued

| | Test | Result |
|---|---|---|
| 13 | D-Mannose | + |
| 14 | L-Sorbose | − |
| 15 | L-Rhamnose | − |
| 16 | Dulcitol | − |
| 17 | Inositol | + |
| 18 | D-Mannitol | + |
| 19 | D-Sorbitol | + |
| 20 | Methyl αD-mannopyranoside | − |
| 21 | Methyl αD-glucopyranoside | + |
| 22 | N-Acetylglucosamine | − |
| 23 | Amygdalin | − |
| 24 | Arbutin | + |
| 25 | Aesculin iron citrate | + |
| 26 | Salicin | + |
| 27 | D-Cellobiose | + |
| 28 | D-Maltose | + |
| 29 | D-Lactose | − |
| 30 | D-Melibiose | + |
| 31 | D-Saccharose | + |
| 32 | D-Trehalose | + |
| 33 | Inulin | + |
| 34 | D-Melezitose | − |
| 35 | D-Raffinose | + |
| 36 | Starch | + |
| 37 | Glycogen | + |
| 38 | Xylitol | − |
| 39 | Gentiobiose | − |
| 40 | D-Turanose | + |
| 41 | D-Lyxose | − |
| 42 | D-Tagatose | − |
| 43 | D-Fucose | − |
| 44 | L-Fucose | − |
| 45 | D-Arabitol | − |
| 46 | L-Arabitol | − |
| 47 | Potassium gluconate | − |
| 48 | Potassium 2-cetogluconate | − |
| 49 | Potassium 5-cetogluconate | − |

3/Strain: NOL 03

Genus and species: *Bacillus subtilis*
Morphology: Gram+ *bacillus* isolated or in twos. Presence of spores in the gram.
Characteristics:
    Culture medium: basic (PCA) or blood agar
    Temperature: 30-37° C.
    Appearance of the colonies on PCA:
        small, flat, irregular edge, darker centre
    Appearance of the colonies on blood agar:
        non-haemolytic, slightly hollow centre, sharp edge
Oxidase test+
Catalase test+

API 50CHB Profile

| | Test | Result |
|---|---|---|
| 1 | Glycerol | + |
| 2 | Erythritol | − |
| 3 | D-Arabinose | − |
| 4 | L-Arabinose | + |
| 5 | D-Ribose | − |
| 6 | D-Xylose | − |
| 7 | L-Xylose | − |
| 8 | D-Adonitol | − |
| 9 | Methyl βD-xylopyranoside | − |
| 10 | D-Galacyose | − |
| 11 | D-Glucose | + |
| 12 | D-Fructose | + |

-continued

| | Test | Result |
|---|---|---|
| 13 | D-Mannose | + |
| 14 | L-Sorbose | − |
| 15 | L-Rhamnose | − |
| 16 | Dulcitol | − |
| 17 | Inositol | + |
| 18 | D-Mannitol | + |
| 19 | D-Sorbitol | + |
| 20 | Methyl αD-mannopyranoside | − |
| 21 | Methyl αD-glucopyranoside | + |
| 22 | N-Acetylglucosamine | − |
| 23 | Amygdalin | + |
| 24 | Arbutin | + |
| 25 | Aesculin iron citrate | + |
| 26 | Salicin | + |
| 27 | D-Cellobiose | + |
| 28 | D-Maltose | + |
| 29 | D-Lactose | − |
| 30 | D-Melibiose | + |
| 31 | D-Saccharose | + |
| 32 | D-Trehalose | + |
| 33 | Inulin | + |
| 34 | D-Melezitose | − |
| 35 | D-Raffinose | + |
| 36 | Starch | + |
| 37 | Glycogen | + |
| 38 | Xylitol | − |
| 39 | Gentiobiose | − |
| 40 | D-Turanose | + |
| 41 | D-Lyxose | − |
| 42 | D-Tagatose | − |
| 43 | D-Fucose | − |
| 44 | L-Fucose | − |
| 45 | D-Arabitol | − |
| 46 | L-Arabitol | − |
| 47 | Potassium gluconate | − |
| 48 | Potassium 2-cetogluconate | − |
| 49 | Potassium 5-cetogluconate | − |

4/Strain: NOL 04

Genus and species: *Bacillus subtilis*
Morphology: Gram+ *bacillus* isolated or in twos
Characteristics:
    Culture medium: basic (PCA) or blood agar
    Temperature: 30-37° C.
    Appearance of the colonies on PCA:
        small, flat, irregular edge, darker centre
    Appearance of the colonies on blood agar:
        haemolytic, irregular edge
Oxidase test+
Catalase test+

API 50CHB Profile

| | Test | Result |
|---|---|---|
| 1 | Glycerol | + |
| 2 | Erythritol | − |
| 3 | D-Arabinose | − |
| 4 | L-Arabinose | + |
| 5 | D-Ribose | +/− |
| 6 | D-Xylose | − |
| 7 | L-Xylose | − |
| 8 | D-Adonitol | − |
| 9 | Methyl βD-xylopyranoside | − |
| 10 | D-Galacyose | − |
| 11 | D-Glucose | + |
| 12 | D-Fructose | + |
| 13 | D-Mannose | + |

-continued

| | Test | Result |
|---|---|---|
| 14 | L-Sorbose | − |
| 15 | L-Rhamnose | − |
| 16 | Dulcitol | − |
| 17 | Inositol | + |
| 18 | D-Mannitol | + |
| 19 | D-Sorbitol | + |
| 20 | Methyl αD-mannopyranoside | − |
| 21 | Methyl αD-glucopyranoside | +/− |
| 22 | N-Acetylglucosamine | − |
| 23 | Amygdalin | +/− |
| 24 | Arbutin | +/− |
| 25 | Aesculin iron citrate | + |
| 26 | Salicin | + |
| 27 | D-Cellobiose | + |
| 28 | D-Maltose | + |
| 29 | D-Lactose | − |
| 30 | D-Melibiose | − |
| 31 | D-Saccharose | + |
| 32 | D-Trehalose | + |
| 33 | Inulin | +/− |
| 34 | D-Melezitose | − |
| 35 | D-Raffinose | +/− |
| 36 | Starch | +/− |
| 37 | Glycogen | +/− |
| 38 | Xylitol | − |
| 39 | Gentiobiose | − |
| 40 | D-Turanose | − |
| 41 | D-Lyxose | − |
| 42 | D-Tagatose | − |
| 43 | D-Fucose | − |
| 44 | L-Fucose | − |
| 45 | D-Arabitol | − |
| 46 | L-Arabitol | − |
| 47 | Potassium gluconate | − |
| 48 | Potassium 2-cetogluconate | − |
| 49 | Potassium 5-cetogluconate | − |

5/Strain: NOL 11

Genus and species: *Lactococcus lactis* spp *lactis* 1
Morphology: Gram+ coccus grouped in twos in small chains
Characteristics:
    Culture medium: MRS
    Temperature: 30-37° C.
    Appearance of the colonies on MRS: small, brown
      blood agar: small, grey
Oxidase test−
Catalase test−

API 50CHL Profile

| | Test | Result |
|---|---|---|
| 1 | Glycerol | − |
| 2 | Erythritol | − |
| 3 | D-Arabinose | − |
| 4 | L-Arabinose | − |
| 5 | D-Ribose | + |
| 6 | D-Xylose | − |
| 7 | L-Xylose | − |
| 8 | D-Adonitol | − |
| 9 | Methyl βD-xylopyranoside | − |
| 10 | D-Galacyose | + |
| 11 | D-Glucose | + |
| 12 | D-Fructose | + |
| 13 | D-Mannose | + |
| 14 | L-Sorbose | − |
| 15 | L-Rhamnose | − |
| 16 | Dulcitol | − |
| 17 | Inositol | − |

-continued

| | Test | Result |
|---|---|---|
| 18 | D-Mannitol | + |
| 19 | D-Sorbitol | − |
| 20 | Methyl αD-mannopyranoside | − |
| 21 | Methyl αD-glucopyranoside | − |
| 22 | N-Acetylglucosamine | + |
| 23 | Amygdalin | − |
| 24 | Arbutin | − |
| 25 | Aesculin iron citrate | + |
| 26 | Salicin | + |
| 27 | D-Cellobiose | + |
| 28 | D-Maltose | + |
| 29 | D-Lactose | − |
| 30 | D-Melibiose | − |
| 31 | D-Saccharose | + |
| 32 | D-Trehalose | + |
| 33 | Inulin | − |
| 34 | D-Melezitose | − |
| 35 | D-Raffinose | − |
| 36 | Starch | + |
| 37 | Glycogen | − |
| 38 | Xylitol | − |
| 39 | Gentiobiose | − |
| 40 | D-Turanose | − |
| 41 | D-Lyxose | − |
| 42 | D-Tagatose | − |
| 43 | D-Fucose | − |
| 44 | L-Fucose | − |
| 45 | D-Arabitol | − |
| 46 | L-Arabitol | − |
| 47 | Potassium gluconate | − |
| 48 | Potassium 2-cetogluconate | − |
| 49 | Potassium 5-cetogluconate | − |

6/Strain: NOL 12

Genus and species: *Pediococcus pentosaceus* 2
Morphology: Gram+ coccus grouped in a pair or in a tetrad
Characteristics:
    Culture medium: MRS
    Temperature: 30-37° C.
    Appearance of the colonies on MRS: white, milky
      blood agar: small, grey
Oxidase test−
Catalase test−

API 50CHL Profile

| | Test | Result |
|---|---|---|
| 1 | Glycerol | − |
| 2 | Erythritol | − |
| 3 | D-Arabinose | − |
| 4 | L-Arabinose | + |
| 5 | D-Ribose | + |
| 6 | D-Xylose | + |
| 7 | L-Xylose | − |
| 8 | D-Adonitol | − |
| 9 | Methyl βD-xylopyranoside | − |
| 10 | D-Galacyose | + |
| 11 | D-Glucose | + |
| 12 | D-Fructose | + |
| 13 | D-Mannose | + |
| 14 | L-Sorbose | − |
| 15 | L-Rhamnose | − |
| 16 | Dulcitol | − |
| 17 | Inositol | − |
| 18 | D-Mannitol | − |
| 19 | D-Sorbitol | − |
| 20 | Methyl αD-mannopyranoside | − |
| 21 | Methyl αD-glucopyranoside | − |

-continued

| Test | | Result |
|---|---|---|
| 22 | N-Acetylglucosamine | + |
| 23 | Amygdalin | + |
| 24 | Arbutin | + |
| 25 | Aesculin iron citrate | + |
| 26 | Salicin | + |
| 27 | D-Cellobiose | + |
| 28 | D-Maltose | + |
| 29 | D-Lactose | − |
| 30 | D-Melibiose | + |
| 31 | D-Saccharose | + |
| 32 | D-Trehalose | + |
| 33 | Inulin | − |
| 34 | D-Melezitose | − |
| 35 | D-Raffinose | + |
| 36 | Starch | − |
| 37 | Glycogen | − |
| 38 | Xylitol | − |
| 39 | Gentiobiose | + |
| 40 | D-Turanose | − |
| 41 | D-Lyxose | − |
| 42 | D-Tagatose | + |
| 43 | D-Fucose | − |
| 44 | L-Fucose | − |
| 45 | D-Arabitol | − |
| 46 | L-Arabitol | − |
| 47 | Potassium gluconate | − |
| 48 | Potassium 2-cetogluconate | − |
| 49 | Potassium 5-cetogluconate | − |

It is to be noted that the biochemical identification of the bacilli on the basis of the API 50CHB profile is not reliable.

Consequently, identification of those bacteria was supplemented by characterisation of their genome (identification by sequencing of the gene coding for 16S RNA).

In the particular case of strain NOL 01, this analysis did not allow the *subtilis* or *licheniformis* species to be differentiated.

However, the appearance of the colonies would tend to indicate *Bacillus licheniformis*.

Five of the six bacterial strains which may be contained in the composition according to the invention have, moreover, been deposited at the Institut Pasteur under the Budapest treaty under the following numbers:

| | |
|---|---|
| NOL 01 | CNCM I - 4606 |
| NOL 03 | CNCM I - 4607 |
| NOL 04 | CNCM I - 4608 |
| NOL 11 | CNCM I - 4609 |
| NOL 12 | CNCM I - 4610 |

The effectiveness of the composition provided by the invention for the treatment of colibacillosis and also the synergy effect of the particular strains of *bacillus* and of lactic acid bacteria have been confirmed by in vitro tests starting from Petri dishes inoculated with *E. coli* and also by in vivo tests conducted on poultry farms.

Example 1: In Vitro Tests

Demonstration of the synergy of a *bacillus* and a lactic acid bacterium in respect of the growth of an *E. coli*.

The following steps were carried out in succession:

Day 1: Subculturing of the strains of *bacillus* and lactic acid bacteria on a blood agar. Incubation of the dishes for 20-24 h at 37° C.

Day 2: Preparation of the Petri dishes Ø 90 mm.

pour 17 ml of supercooled PCA into a Petri dish and allow to cool remove the PCA over a width of 4 mm (with the aid of the tip of a Pasteur pipette) and a length of ½ the central strip. Replace it with supercooled MRS and allow to cool.

First inoculation of the Petri dishes:

inoculation of a lactic acid bacterium on the central ½ strip of MRS inoculation of a *bacillus* as a continuation of the ½ strip of the lactic acid bacterium incubation for 20-24 h at 37° C.

Subculture the strains of *E. coli* on a Drigalski agar and incubate for 20-24 h at 37° C.

Day 3: Preparation of the suspension of *E. coli*:

from the *E. coli* colonies on Drigalski agar, prepare a suspension of 0.5 McFarland in saline solution dilute 230 µl of the suspension in 4.2 ml of saline solution.

Second inoculation of the Petri dishes:

with the aid of a swab and starting from the *E. coli* dilution, paint the dishes on each side of the strips of *bacillus* and lactic acid bacterium incubate for 48 h at 37° C.

Day 5: Measurement (in mm) of the width of the zones of inhibition of the growth of *E. coli*:

ZI lactic=zone of total inhibition created by the lactic acid bacterium (caused principally by its acidifying activity, which modifies the medium, and not by the bacterium itself)

ZI *bacillus*=zone of total inhibition created by the *bacillus*

ZI synergy=zone of total inhibition created by the association of the *bacillus* and the lactic acid bacterium A Petri dish 1 prepared in the manner mentioned above is shown schematically in FIG. 1.

Reference numeral 2 corresponds to the band of MRS on which a strip 3 of a lactic acid bacterium is inoculated.

Reference numeral 4 corresponds to a strip of *bacillus* inoculated on the PCA as a continuation of the strip of lactic acid bacterium.

The shaded part with reference numeral 5 corresponds to the zone of growth of *E. coli*, while the white zones on either side of the strips 3, 4 correspond to the zones of total inhibition of that growth.

The measurement points of the width of the zones of inhibition of the growth of *E. coli*: ZI lactic, ZI synergy and ZI *bacillus*, are indicated by double arrows.

This figure clearly shows the synergy effect between a *bacillus* and a lactic acid bacterium.

The inhibition of the growth of two strains A and B of *E. coli* by virtue of the synergy between the different strains of *bacillus* and lactic acid bacteria can be shown in the table below.

| INOCULATION | | | INHIBITION ZONE (mm) | | |
|---|---|---|---|---|---|
| bacillus | lactic | E. coli | lactic (acidity) | bacillus | SYNERGY |
| NOL 01 | NOL 11 | A | 1 | 0 | 3 |
| | | B | 1 | 0 | 4 |
| NOL 01 | NOL 12 | A | 13 | 2 | 3 |
| | | B | 14 | 0 | 3 |
| NOL 02 | NOL 11 | A | 1 | 2 | 0 |
| | | B | 1 | 2 | 0 |
| NOL 02 | NOL 12 | A | 10 | 3 | 0 |
| | | B | 12 | 3 | 0 |
| NOL 03 | NOL 11 | A | 1 | 0 | 5 |
| | | B | 2 | 0 | 6 |

-continued

| INOCULATION | | INHIBITION ZONE (mm) | | | |
|---|---|---|---|---|---|
| bacillus | lactic | E. coli | lactic (acidity) | bacillus | SYNERGY |
| NOL 03 | NOL 12 | A | 12 | 0 | 5 |
|  |  | B | 15 | 0 | 5 |
| NOL 04 | NOL 12 | A | 10 | 0 | 3 |
|  |  | B | 14 | 0 | 5 |

These results show that the zones of total inhibition of the *bacillus* on the growth of *E. coli* are small and different according to the strains.

In synergy with a lactic acid bacterium, the zones of total inhibition increase markedly in the case of bacilli NOL 01, NOL 03 and NOL 04, which exhibit very little activity individually.

This synergy between a *bacillus* and a lactic acid bacterium is particularly pronounced in the case of *bacillus* NOL 03.

Unlike the other three strains, *bacillus* NOL 02 loses its inhibitory activity in respect of the growth of *E. coli*.

Example 2: In Vivo Tests

Within the scope of these tests, bottles containing the following preparations were prepared beforehand:
Preparation 1=20 ml bottle
 mixture of 4 bacilli NOL 01, NOL 02, NOL 03, NOL 04 (in vegetative form)
 concentration from $10^5$ to $10^8$ cfu/ml
 storage between −80° C. and −21° C.
Preparation 2=20 ml bottle
 mixture of 2 lactic acid bacteria (*lactococcus+pediococcus*)
 concentration from $10^9$ to $10^{10}$ cfu/ml
 storage between −80° C. and −21° C.
Preparation 3=20 ml bottle
 1 *bacillus* (NOL 04) (in vegetative form)
 concentration from $10^5$ to $10^8$ cfu/ml (revivifiable forms)
 storage between −80° C. and −21° C.
The following mixtures were then tested in the field:
dose of mixture 1: 1 bottle of preparation 1+1 bottle of preparation 2
dose of mixture 2: 1 bottle of preparation 1+1 bottle of preparation 2

Example 2.1: Test of Treatment with Mixture 1 on Laying Hens

Farm: building with 56,000 hens
Laboratory test at 28 weeks: LA17656
Bacteriology: isolation of an *E. coli* of serotype O78K80
Treatment:
 5 doses per day for 4 days in drinking water on battery no. 5
 5 doses per day for 4 days nebulised through the whole building
 (5 doses for 12,000 hens (battery no. 5)→25 tonnes, i.e. 2 doses per 10 tonnes)
The change in the mortality is shown in the table below and in FIG. 2.1

| AGE (days) | Mortality | Treatment (dose) |
|---|---|---|
| 190 | 62 |  |
| 191 | 57 |  |
| 192 | 68 |  |
| 193 | 72 |  |
| 194 | 81 |  |
| 195 | 75 |  |
| 196 | 80 | 5 |
| 197 | 66 | 5 |
| 198 | 37 | 5 |
| 199 | 21 | 5 |
| 200 | 13 |  |
| 201 | 10 |  |
| 202 | 12 |  |
| 203 | 13 |  |
| 204 | 8 |  |
| 205 | 11 |  |

Example 2.2: Test of Treatment with Mixture 1 on Standard Broiler Chickens

Farm: building with 22,500 chickens
Laboratory test at 3 days: LA17656
Post-mortem: omphalitis
Bacteriology: isolation of an *E. coli* of serotype O78K80
Treatments from day 1 to day 2: enrofloxacin→failure of the treatment explained by the result of the test performed on d3 (*E. coli* O78K80 is resistant to enrofloxacin)
Following the test: 2 doses of mixture 1 per day for 3 days in drinking water (2 doses for 22,500 chickens weighing 100 g→2.2 tonnes, i.e. 1 dose per tonne).
The change in the mortality from day 1 to day 5 is shown in the table below and in FIG. 2.2.

| AGE (days) | Mortality | Treatment (dose) |
|---|---|---|
| 1 | 0 |  |
| 2 | 50 |  |
| 3 | 195 | 2 |
| 4 | 93 | 2 |
| 5 | 30 | 2 |

Example 2.3: Test of Treatment with Mixture 2 on Standard Broiler Turkeys

Farm: building with 9000 turkeys
Laboratory test at 56 days: LA19492
Post-mortem: respiratory colibacillosis lesions
Bacteriology: isolation of an *E. coli* of serotype (O78K80; O2; O1) negative
Treatment: 4 doses of mixture 2 per day for 4 days in drinking water (4 doses for 9000 turkeys weighing 3.9 kg→35 tonnes, i.e. 1 dose for 10 tonnes).
The change in the mortality between days 51 and 59 is shown in the table below and in FIG. 2.3.

| AGE (days) | Mortality | Treatment (dose) |
|---|---|---|
| 51 | 3 |  |
| 52 | 4 |  |
| 53 | 5 |  |
| 54 | 6 |  |
| 55 | 8 |  |

-continued

| AGE (days) | Mortality | Treatment (dose) |
|---|---|---|
| 56 | 8 | 4 |
| 57 | 4 | 4 |
| 58 | 1 | 4 |
| 59 | 1 | 4 |

Example 2.4: Test of Treatment with Mixture 1 on Standard Broiler Chickens

Farm: building with 20,000 chickens
Laboratory test at 32 days: LA18574
Post-mortem: pericarditis/arthritis/necrosis of the femur head
Bacteriology: isolation of an *E. coli* of serotype (O78K80; O2; O1) negative
Treatment: 4 doses of mixture 1 per day for 4 days (4 doses for 20,000 chickens weighing 1.4 kg→28 tonnes, i.e. 1.5 doses per 10 tonnes).
The change in the mortality between days 30 and 39 is shown in the table below and in FIG. 2.4.
Standard well-being mortality: 1%+0.06%×N (N=number of days' rearing)
3.4% (with N=40 days' rearing)
that is to say, a total mortality of 680 deaths (20,000 chickens×3.4%)
that is to say, an average daily mortality of 17 deaths (680 deaths/40 days)

| AGE (days) | Mortality | | Treatment (dose) |
|---|---|---|---|
| | Standard (average) | Actual | |
| 30 | 17 | 31 | |
| 31 | 17 | 47 | |
| 32 | 17 | 61 | |
| 33 | 17 | 101 | 4 |
| 34 | 17 | 74 | 4 |
| 35 | 17 | 43 | 4 |
| 36 | 17 | 27 | 4 |
| 37 | 17 | 29 | |
| 38 | 17 | 43 | |
| 38 | 17 | 45 | |

These results clearly prove the effectiveness of the composition provided by the invention for the treatment of colibacillosis.

The invention claimed is:

1. A bacterial composition, comprising at least one strain of *Bacillus* and at least one lactic acid bacterium, wherein said *Bacillus* is selected from the group consisting of: NOL01, NOL02, NOL03, and NOL04, and said lactic acid bacterium is selected from the group consisting of: *Lactococcus lactis* spp *lactis* 1 strain NOL11 and *Pediococcus pentosaceus* 2 strain NOL12, wherein said bacterial composition comprises at least about $10^5$ cfu/ml of said *Bacillus* and at least about $10^5$ cfu/ml of said lactic acid bacteria.

2. The bacterial composition according to claim 1, wherein said bacterial composition comprises between $10^5$ and $10^9$ cfu/ml of said *Bacillus* and between $10^9$ and $10^{10}$ cfu/ml of said lactic acid bacteria.

3. The bacterial composition according to claim 1, wherein said composition is in sporulated form, in vegetative form, or in a mixture of both sporulated and vegetative form.

4. The bacterial composition according to claim 1, wherein the composition comprises at least one of the compositions selected from the group consisting of:
   the strain NOL 01 and the strain NOL 11;
   the strain NOL 01 and the strain NOL 12;
   the strain NOL 02 and the strain NOL 11;
   the strain NOL 02 and the strain NOL 12;
   the strain NOL 03 and the strain NOL 11;
   the strain NOL 03 and the strain NOL 12;
   the strain NOL 04 and the strain NOL 12; and
   the strains NOL 01, NOL 02, NOL 03 and NOL 04, at a concentration from $10^5$ to $10^8$ cfu/ml and the strains NOL 11 and NOL12 at a concentration from $10^9$ to $10^{10}$ cfu/ml.

5. The bacterial composition according to claim 1, wherein:
   the strain NOL 01 is the strain deposited at the Institut Pasteur under the Budapest treaty under the number CNCM I-4606;
   the strain NOL 03 is the strain deposited at the Institut Pasteur under the Budapest treaty under the number CNCM I-4607;
   the strain NOL 04 is the strain deposited at the Institut Pasteur under the Budapest treaty under the number CNCM I-4608;
   the strain NOL 11 is the strain deposited at the Institut Pasteur under the Budapest treaty under the number CNCM I-4609; and
   the strain NOL 12 is the strain deposited at the Institut Pasteur under the Budapest treaty under the number CNCM I-4610.

6. A method for treating colibacillosis infections in animal farms, comprising the steps of:
   administering to an animal of an effective amount of a bacterial composition, wherein said bacterial composition comprises at least $10^5$ cfu/ml of at least one of the strain of *Bacillus* strains selected from the group consisting of: NOL01, NOL02, NOL03 and NOL04, and at least $10^5$ cfu/ml of at least one lactic acid bacterium selected from the group consisting of: *Lactococcus lactis* spp *lactis* 1 strain NOL11 and *Pediococcus pentosaceus* 2 strain NOL12.

7. The method of claim 6, wherein said bacterial composition comprises between $10^5$ and $10^9$ cfu/ml of *bacillus* and between $10^9$ and $10^{10}$ cfu/ml of lactic acid bacteria.

8. The method of claim 6, wherein said bacterial composition is in sporulated form, in vegetative form, or in a mixture of sporulated and vegetative form.

9. The method of claim 6, wherein said bacterial composition comprises at least one of the compositions selected from the group consisting of:
   the strain NOL 01 and the strain NOL 11;
   the strain NOL 01 and the strain NOL 12;
   the strain NOL 02 and the strain NOL 11;
   the strain NOL 02 and the strain NOL 12;
   the strain NOL 03 and the strain NOL 11;
   the strain NOL 03 and the strain NOL 12;
   the strain NOL 04 and the strain NOL 12; and
   the strains NOL 01, NOL 02, NOL 03 and NOL 04, at a concentration from $10^5$ to $10^8$ cfu/ml and the strains NOL 11 and NOL12 at a concentration from $10^9$ to $10^{10}$ cfu/ml.

10. The method of claim 6, wherein:
   the strain NOL 01 is the strain deposited at the Institut Pasteur under the Budapest treaty under the number CNCM I-4606;

the strain NOL 03 is the strain deposited at the Institut Pasteur under the Budapest treaty under the number CNCM I-4607;

the strain NOL 04 is the strain deposited at the Institut Pasteur under the Budapest treaty under the number CNCM I-4608;

the strain NOL 11 is the strain deposited at the Institut Pasteur under the Budapest treaty under the number CNCM I-4609; and the strain NOL 12 is the strain deposited at the Institut Pasteur under the Budapest treaty under the number CNCM I-4610.

11. The method of claim 6, wherein the animal farm is a poultry farm.

12. The method of claim 6, further comprising the step of: adding said bacterial composition to a drinking water.

13. A drinking water for a farm animal, comprising:
an effective amount of water; and
a bacterial composition, comprising at least $10^5$ cfu/ml of at least one *Bacillus* selected from the group consisting of: NOL01, NOL02, NOL03 and NOL04; and at least $10^5$ cfu/ml of at least one lactic acid bacterium selected from the group consisting of: *Lactococcus lactis* spp *lactis* 1 strain NOL11 and *Pediococcus pentosaceus* 2 strain NOL12.

14. The drinking water according to claim 13, wherein said bacterial composition comprises at least one of the compositions selected from the group consisting of:

the strain NOL 01 and the strain NOL 11;
the strain NOL 01 and the strain NOL 12;
the strain NOL 02 and the strain NOL 11;
the strain NOL 02 and the strain NOL 12;
the strain NOL 03 and the strain NOL 11;
the strain NOL 03 and the strain NOL 12;
the strain NOL 04 and the strain NOL 12; and
the strains NOL 01, NOL 02, NOL 03 and NOL 04, at a concentration from $10^5$ to $10^8$ cfu/ml and the strains NOL 11 and NOL 12 at a concentration from $10^9$ to $10^{10}$ cfu/ml.

15. The drinking water according to claim 13, wherein:
the strain NOL 01 is the strain deposited at the Institut Pasteur under the Budapest treaty under the number CNCM I-4606;

the strain NOL 03 is the strain deposited at the Institut Pasteur under the Budapest treaty under the number CNCM I-4607;

the strain NOL 04 is the strain deposited at the Institut Pasteur under the Budapest treaty under the number CNCM I-4608;

the strain NOL 11 is the strain deposited at the Institut Pasteur under the Budapest treaty under the number CNCM I-4609; and the strain NOL 12 is the strain deposited at the Institut Pasteur under the Budapest treaty under the number CNCM I-4610.

\* \* \* \* \*